US012780823B2

(12) United States Patent
Avva et al.

(10) Patent No.: US 12,780,823 B2
(45) Date of Patent: Nov. 3, 2026

(54) PROCESS FOR THE PURIFICATION OF MITRAGYNINE

(71) Applicant: LUCKY 4U EXIMS, Tirupati (IN)

(72) Inventors: Surya Pavan Kumar Avva, Tirupati (IN); V.S.R. Suresh Mamidipalli, Tirupati (IN)

(73) Assignee: LUCKY 4U EXIMS, Andhra Pradesh (IN)

( * ) Notice: Subject to any disclaimer, the term of this patent is extended or adjusted under 35 U.S.C. 154(b) by 728 days.

(21) Appl. No.: 18/311,744

(22) Filed: May 3, 2023

(65) Prior Publication Data

US 2024/0287069 A1 Aug. 29, 2024

(30) Foreign Application Priority Data

Feb. 17, 2023 (IN) ............................. 202341010947

(51) Int. Cl.
*C07D 471/14* (2006.01)

(52) U.S. Cl.
CPC .................................. *C07D 471/14* (2013.01)

(58) Field of Classification Search
None
See application file for complete search history.

(56) References Cited

PUBLICATIONS

American Chemical Society. Chemical Abstract Service. RN 11047-41-9. Entered into STN: Nov. 16, 1984. (Year: 1984).*

Goh et al. "A Simple and Cost Effective Isolation and Purification Protocol of Mitragynine From Mitragyna Speciosa Korth (Ketum) Leaves." The Malaysian Journal of Analytical Sciences. Jan. 2011. vol. 15, No. 1. pp. 54-60.

Boffa et al. "Alkaloid Profiles and Activity in Different Mitragyna speciosa Strains." Natural Product Communications. 2018. vol. 13, No. 9. pp. 1111-1116.

Mustafa et al. "Enhancing extraction yield and purity of Mitragynine from Mitragyna speciosa through sequential solvent extraction and characterisation using NMR technique." International Journal of Scientific & Technology Research. Mar. 2020. vol. 9, Issue 3. pp. 3846-3854.

Orio et al. "UAE, MAE, SFE-CO2 and classical methods for the extraction of Mitragyna speciosa leaves." Ultrasonics Sonochemistry. 2012. vol. 19. pp. 591-595.

Amrianto et al. "Mitragynine: a review of its extraction, identification, and purification methods." Current Research on Biosciences and Biotechnology. 2021. vol. 3, Issue 1. pp. 165-171.

* cited by examiner

*Primary Examiner* — John S Kenyon

(74) *Attorney, Agent, or Firm* — McCormick, Paulding & Huber PLLC

(57) ABSTRACT

The present invention discloses an improved process for the purification of Mitragynine or the preparation of purified Mitragynine salt, particularly purification of Mitragynine or the preparation of purified Mitragynine salt for the pharmaceutical preparations. More particularly the present invention discloses purification of Mitragynine or the preparation of purified Mitragynine salt using alcohol.

29 Claims, 3 Drawing Sheets

Sample Information

| | |
|---|---|
| Acquired by | : Admin |
| Sample Name | : 22-09-027-X-75-SA-A-1 |
| Sample ID | : |
| Tray# | : 1 |
| Vail# | : 13 |
| Injection Volume | : 10 uL |
| Data Filename | : 22-09-027-X-75-SA-A-1.lcd |
| Method Filename | : Mitragynine.lcm |
| Batch Filename | : 201122.lcb |
| Report Filename | : mitrya.lcr |
| Date Acquired | : 20-Nov-22 6:45:23 PM |
| Data Processed | : 29-Nov-22 9:58:13 PM |

Chromatogram
22-09-027-X-75-SA-A-1 D:\LC-Solution\Data\2022-HPLC-1\NOV-11\201122\22-09-027-X-75-SA-A-1.lcd
-------

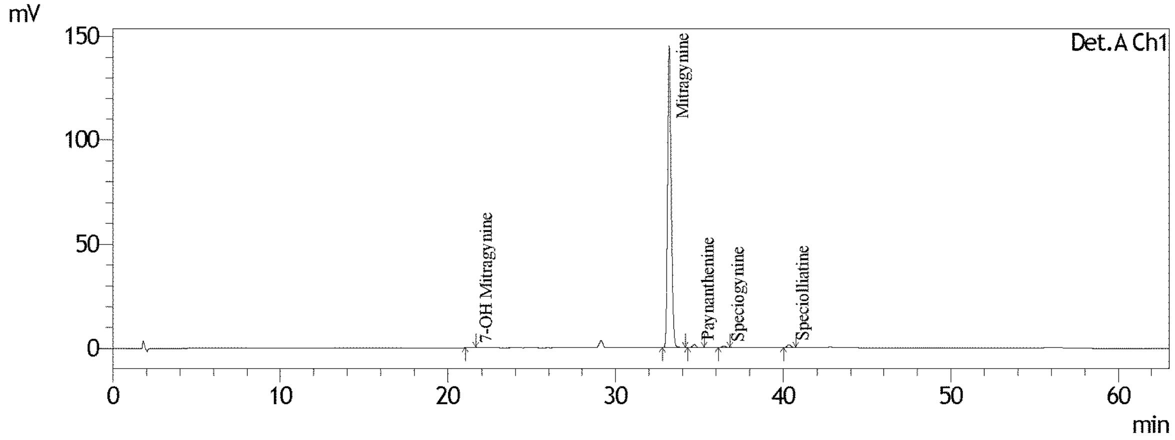

1 Det.A Ch1 / 254nm

PeakTable D:\LC-Solution\Data\2022-HPLC-1\NOV-11\201122\22-09-027-X-75-SA-A-1.lcd
Detector A Ch1 254nm

| Peak# | Name | Area | Height | Area % | Height % |
|---|---|---|---|---|---|
| 1 | 7-OH Mitragynine | 719 | 37 | 0.033 | 0.025 |
| 2 | Mitragynine | 2138899 | 144943 | 97.741 | 97.693 |
| 3 | Paynanthenine | 19445 | 1375 | 0.889 | 0.927 |
| 4 | Speciogynine | 10604 | 753 | 0.485 | 0.508 |
| 5 | Speciolliatine | 18662 | 1258 | 0.853 | 0.848 |
| Total | | 2188330 | 148366 | 100.000 | 100.000 |

Figure 1

Sample Information

| | |
|---|---|
| Acquired by | : Admin |
| Sample Name | : 22-09-027-X-75-SA-B-1 |
| Sample ID | : |
| Tray# | : 1 |
| Vail# | : 14 |
| Injection Volume | : 10 uL |
| Data Filename | : 22-09-027-X-75-SA-B-1.lcd |
| Method Filename | : Mitragynine.lcm |
| Batch Filename | : 201122.lcb |
| Report Filename | : mitrya.lcr |
| Date Acquired | : 20-Nov-22 7:52:12 PM |
| Data Processed | : 29-Nov-22 10:05:33 PM |

Chromatogram
22-09-027-X-75-SA-B-1 D:\LC-Solution\Data\2022-HPLC-1\NOV-11\201122\22-09-027-X-75-SA-B-1.lcd

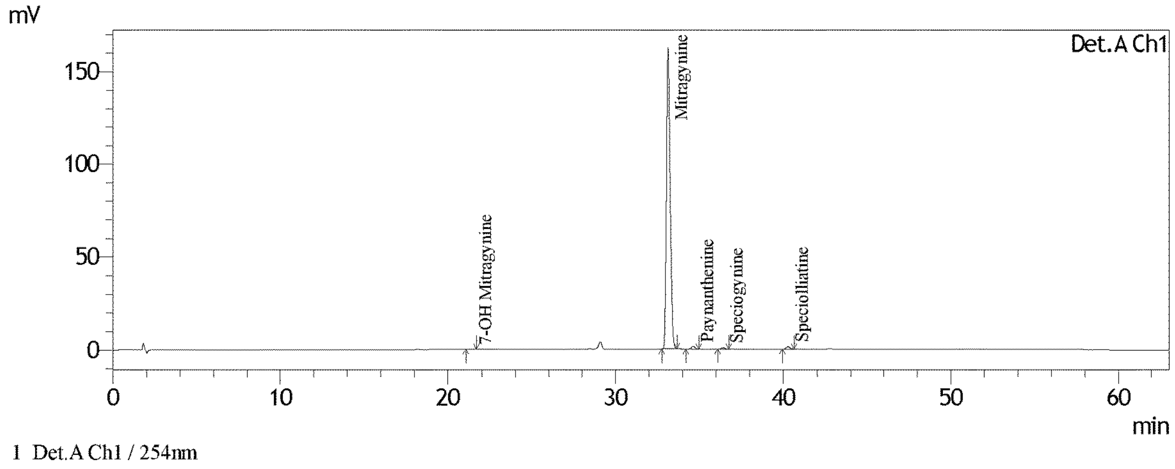

PeakTable D:\LC-Solution\Data\2022-HPLC-1\NOV-11\201122\22-09-027-X-75-SA-B-1.lcd
Detector A Ch1 254nm

| Peak# | Name | Area | Height | Area % | Height % |
|---|---|---|---|---|---|
| 1 | 7-OH Mitragynine | 761 | 49 | 0.030 | 0.029 |
| 2 | Mitragynine | 2460145 | 162496 | 97.908 | 97.781 |
| 3 | Paynanthenine | 21503 | 1525 | 0.856 | 0.917 |
| 4 | Speciogynine | 10192 | 735 | 0.406 | 0.442 |
| 5 | Speciolliatine | 20100 | 1380 | 0.800 | 0.830 |
| Total | | 2512701 | 166183 | 100.000 | 100.000 |

Figure 2

Sample Information

| | |
|---|---|
| Acquired by | : Admin |
| Sample Name | : 22-10-031-X-75-SA-A-1 |
| Sample ID | : |
| Tray# | : 1 |
| Vail# | : 11 |
| Injection Volume | : 10 uL |
| Data Filename | : 22-10-031-X-75-SA-A-1.lcd |
| Method Filename | : Mitragynine.lcm |
| Batch Filename | : 051222.lcb |
| Report Filename | : mitrya.lcr |
| Date Acquired | : 05-Dec-22 9:54:07 PM |
| Data Processed | : 06-Dec-22 7:09:01 AM |

Chromatogram
22-10-031-X-75-SA-A-1 D:\LC-Solution\Data\2022-HPLC-1\DEC-12\051222\22-10-031-X-75-SA-A-1.lcd

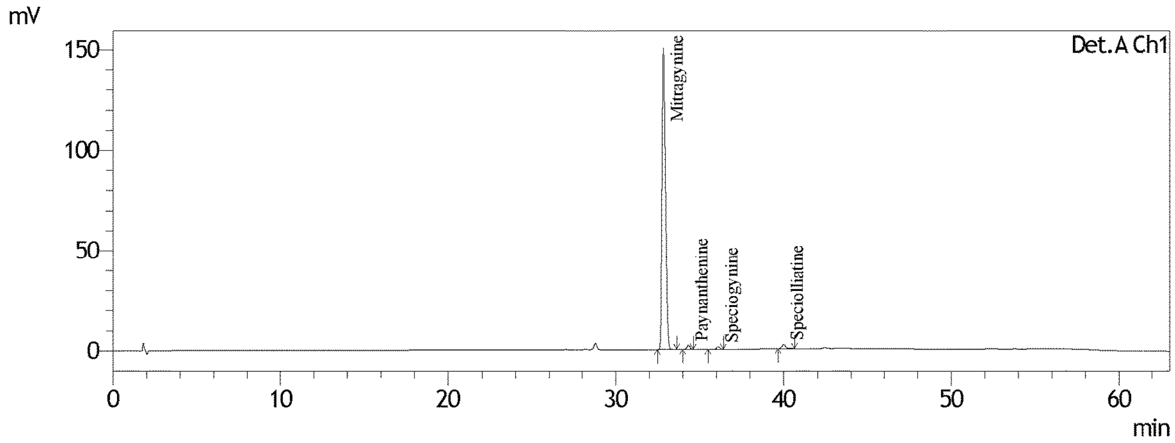

1 Det.A Ch1 / 254nm

PeakTable D:\LC-Solution\Data\2022-HPLC-1\DEC-12\051222\22-10-031-X-75-SA-A-1.lcd
Detector A Ch1 254nm

| Peak# | Name | Area | Height | Area % | Height % |
|---|---|---|---|---|---|
| 1 | Mitragynine | 2100102 | 150099 | 96.467 | 96.432 |
| 2 | Paynanthenine | 26414 | 2146 | 1.213 | 1.379 |
| 3 | Speciogynine | 16844 | 1308 | 0.774 | 0.840 |
| 4 | Speciolliatine | 33667 | 2100 | 1.546 | 1.349 |
| Total | | 2177027 | 155653 | 100.000 | 100.000 |

Figure 3

PROCESS FOR THE PURIFICATION OF MITRAGYNINE

CROSS-REFERENCE TO RELATED APPLICATION

This application claims foreign priority benefits under 35 U.S.C. § 119 from Indian patent application Ser. No. 202341010947, filed Feb. 17, 2023, the content of which is hereby incorporated by reference in its entirety.

TECHNICAL FIELD

The present invention relates to an improved process for the purification of Mitragynine or the preparation of purified Mitragynine salt, particularly purification of Mitragynine or the preparation of purified Mitragynine salt for the pharmaceutical preparations. More particularly, present invention relates to purification of Mitragynine or the preparation of purified Mitragynine salt using alcohol.

BACKGROUND

Mitragynine is the main indole alkaloids commonly found in the leaves of *Mitragyna speciosa*. It was first isolated in 1921 and its chemical structure was fully elucidated in 1964.

Mitragynine is chemically known as methyl (E)-2-[(2S,3S,12bS)-3-ethyl-8-methoxy-1,2,3,4,6,7,12,12b-octahydroindolo[2,3-a]quinolizin-2-yl]-3-methoxyprop-2-enoate.

The chemical structure of Mitragynine is represented as:

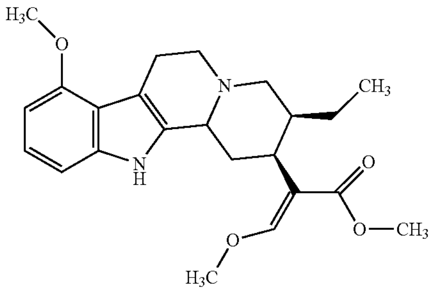 [SMILES: CC[C@@H]1CN2CCc3c([nH]c4cccc(OC)c34)C2C[C@@H]1/C(=C\OC)C(=O)OC]

Mitragynine possesses several pharmacological properties such as antinociceptive and anti-inflammatory.

Currently there are several methods available for the extraction and isolation of Mitragynine from *Mitragyna speciosa* leaves. These extraction and isolation methods available in the market have their own advantages and disadvantages. In addition to this it is also important to obtain the pure compound to avoid undesirable impurities obtained in the extraction process, since these undesirable impurities have side effects on the pharmacological applications. Some of the processes known in art are mentioned below:

Goh Teik Beng et. al., *A simple and cost-effective isolation and purification protocol of Mitragynine from Mitragyna speciosa Korth (Ketum) leaves, The Malaysian Journal of Analytical Sciences, Vol* 15 *No* 1, 54-60, 2011, states that purification method such as acidification or neutralization processes are needed to obtain pure Mitragynine.

Luisa Boffa et. al., *Alkaloid Profiles* and *Activity in Different Mitragyna speciosa* Strains, *Natural Product Communications Vol.* 13 (9) 2018, discloses extraction and purification of various alkaloids from different *Mitragyna speciosa* strains which includes extraction of *M. speciosa* leaves with a mixture of methanol and water with the help of a magnetic stirrer at room temperature for 24 hours. This is followed by purification including several steps using either an alkaline phase or an acid phase ending with precipitation at pH 9 (ammonium hydroxide solution). The residue and alkaline solution were rinsed with Dichloromethane.

Radhiahtul Raehan Mustafa et. al., *Enhancing extraction yield and purity of Mitragynine from Mitragyna speciosa through sequential solvent extraction and characterisation using NMR technique. Int J Sci Technol Res* 9(3): 3846-54, March 2020, discloses separation of Mitragynine from the crude hexane-chloroform-MeOH extract using silica gel column chromatography. The solvent system used in column chromatography is hexane: EtOAc. Approximately 1.0 g of the crude extract was purified using column chromatography.

Laura Orio et. al., *UAE, MAE, SFE-CO2 and classical methods for the extraction of Mitragyna speciosa leaves, Ultrasonics Sonochemistry* 19, 591-595, 2012, discloses Mitragynine purification method using flash chromatography using petroleum ether and ethyl acetate as eluent, on a 4 g silica gel column with a flow rate of 18 ml/min and detected at UV 254 nm. The fraction containing the Mitragynine was collected, and the solvent was removed using rotary evaporator.

Although the prior art discloses various techniques and methods for purification of Mitragynine, these purification processes have setback as these are poorly designed, are time consuming or have many steps or involves use of expensive instruments in the purification process. This results in potential sample losses and poor accuracy.

By aforementioned facts, there exists a need for development of a faster, more economical, simple and commercially significant process for purification of Mitragynine.

SUMMARY

The primary object of the present invention is to provide an improved process for the purification of Mitragynine.

Another object of the invention is to provide a process for the preparation of purified Mitragynine salt.

Another object of the invention is to provide a process for purification of Mitragynine or the preparation of purified Mitragynine salt using alcohol.

Further object of the present invention is to provide a high purity Mitragynine oxalate salt for pharmaceutical applications.

Yet another object of the invention is to provide a process to give improved yield of Mitragynine oxalate salt (25%) with purity of 72-78% by HPLC.

Recognizing the prior arts and need for improved process for purification of Mitragynine, in one aspect accordingly the present invention provides a process for the purification of Mitragynine comprising the steps of:

(a) adding crude extract of Mitragynine to a solvent in a reactor;
(b) stirring the mixture obtained in step (a);
(c) filtering the stirred solution obtained in step (b) to obtain filtered solution and spent;
(d) optionally, adding solvent to the spent obtained in step (c), followed by stirring and filtering, to obtain filtered solution;
(e) loading the filtered solution obtained in step (c) and/or step (d) into the reactor;
(f) adding a mixture of an acid and solvent to the filtered solution in the reactor of step (e);

(g) stirring the solution of step (f) until Mitragynine salt precipitate is formed;
(h) filtering the precipitated salt as obtained in step (g) followed by washing with solvent; and
(i) purifying the salt as obtained in step (h) with alcohol, followed by stirring, filtering and drying to form purified Mitragynine salt.

In step (b) of the present process, the stirring is carried out for 2 hours at 30-50 RPM.

In step (c) of the present process, filtering is carried out through cleaned nutsche filter on 5 microns cloth.

In the said process the acid in step (f) is organic or mineral acid.

The mixture of organic or mineral acid and solvent in the step (f) of the present process is prepared by dissolving the organic or mineral acid slowly into the solvent with continuous mixing followed by stirring at 30-50 RPM for 1 hour and filtering which is carried out through 100 mesh cloth.

The organic or mineral acid employed in step (f) of the present process is selected from a group comprising of hydrochloric acid, hydrobromic acid, perchloric acid, sulphuric acid, oxalic acid, tartaric acid, citric acid, formic acid, trifluoro acetic acid, trichloro acetic acid, or mixture thereof, preferably the organic or mineral acid is oxalic acid.

The solvent employed in steps (a), (d), (f) and (h) of the present process is organic solvent selected from a group comprising of chloroform, acetone, methanol, ethanol, n-butanol, isopropyl alcohol, ethyl acetate, diethyl ether, n-hexane, methylene dichloride, ethylene dichloride or mixture thereof, preferably the solvent is acetone.

In step (g) of the present process, the stirring is carried out for 2 hours at 30-50 RPM.

The Mitragynine salt precipitate formed in step (g) of the present process is hydrochloride salt, hydrobromide salt, perchlorate salt, sulphate salt, oxalate salt, tartrate salt, citrate salt, formate salt, trifluoro acetate salt, or trichloro acetate salt.

Preferably the Mitragynine salt precipitate formed in step (g) of the present process is Mitragynine oxalate salt precipitate.

In step (i) of the present process, alcohol is the dilute alcohol.

The alcohol employed in step (i) of the present process is selected from a group comprising of methanol, ethanol, propanol, butanol or mixture thereof, preferably the alcohol is methanol.

More preferably, in step (i) of the present process the alcohol is 10% methanol.

In step (i) of the present process, the stirring is carried out for 1 hour at 30-50 RPM.

In step (i) of the present process, the salt product obtained after filtration is air dried for 5-6 hours followed by drying in Vacuum Tray Dryer at 45-50° C. under 700 mm of Hg. The purified Mitragynine salt obtained in step (i) of the present process is purified Mitragynine hydrochloride salt, purified Mitragynine hydrobromide salt, purified Mitragynine perchlorate salt, purified Mitragynine sulphate salt, purified Mitragynine oxalate salt, purified Mitragynine tartrate salt, purified Mitragynine citrate salt, purified Mitragynine formate salt, purified Mitragynine trifluoro acetate salt, or purified Mitragynine trichloro acetate salt, preferably the purified Mitragynine salt is purified Mitragynine oxalate salt.

In some embodiment of the invention, there is provided a process for the purification of Mitragynine, said process comprises the steps of:

(a) adding crude extract of Mitragynine to acetone in the reactor;
(b) stirring the mixture obtained in step (a) for 2 hours at 30-50 RPM;
(c) filtering the stirred solution as obtained in step (b) to obtain filtered solution and spent;
(d) optionally, adding acetone to the spent obtained in step (c), followed by stirring and filtering, to obtain filtered solution;
(e) loading the filtered solution obtained in step (c) and/or step (d) into the reactor;
(f) adding a mixture of oxalic acid and acetone to the filtered solution in the reactor of step (e);
(g) stirring the solution of step (f) for 2 hours at 30-50 RPM, until Mitragynine oxalate salt precipitate is formed;
(h) filtering the precipitated Mitragynine oxalate salt as obtained in step (g) followed by washing with acetone; and
(i) purifying the Mitragynine oxalate salt as obtained in step (h) with 10% Methanol, followed by stirring for 1 hour at 30-50 RPM, filtering and drying to form purified Mitragynine oxalate salt.

The mixture of oxalic acid and acetone in step (f) of the above process is prepared by slowly adding oxalic acid to the acetone with continuous mixing followed by stirring for 1 hour at 30-50 RPM and filtering through 100 mesh cloth.

In step (i) of the above process, the salt product obtained after filtration is air dried for 5-6 hours followed by drying in Vacuum Tray Dryer at 45-50° C. under 700 mm of Hg.

The obtained Mitragynine oxalate salt in the present process is in amorphous form.

The instant process provides improved yield of Mitragynine oxalate salt (25%) with purity of 72-78% by HPLC.

In some embodiment of the invention, highly pure Mitragynine oxalate salt obtained according to present invention is suitable for the pharmaceutical preparations.

BRIEF DESCRIPTION OF THE DRAWINGS

FIG. 1 depicts an HPLC graph showing purity of obtained Mitragynine salt.

FIG. 2 depicts an HPLC graph showing purity of obtained Mitragynine salt.

FIG. 3 depicts an HPLC graph showing purity of obtained Mitragynine salt.

DETAILED DESCRIPTION

The following detailed description refers to the accompanying drawing that show, by way of illustration, specific details and embodiments in which the invention may be practised. These embodiments are described in sufficient detail to enable those skilled in the art to practise the invention. Other embodiments may be utilized, and changes may be made without departing from the scope of the invention. The various embodiments are not necessarily mutually exclusive, as some embodiments can be combined with one or more other embodiments to form new embodiments.

Unless defined otherwise, all technical and scientific terms used herein have the same meaning as commonly understood by one of ordinary skill in the art to which the methods belong.

Further the embodiments described herein can be understood more readily by reference to the following detailed description, examples, and drawings. Methods described herein are merely illustrative of the principles of the present invention and are not limited to the specific embodiments presented in the detailed description, examples, and drawings. Numerous modifications and adaptations will be readily apparent to those of skill in the art without departing from the spirit and scope of the invention.

Where a range of values is provided, it is understood that each intervening value between the upper and lower limit of that range and any other stated or intervening value in that stated range, is encompassed within by the methods. The upper and lower limits of these smaller ranges may independently be included in the smaller ranges and are also encompassed within by the methods, subject to any specifically excluded limit in the stated range. Where the stated range includes one or both of the limits, ranges excluding either or both of those included limits are also included in the methods.

Conventional processes for purification of Mitragynine suffers from disadvantages such as time-consuming process, have many steps, involves use of expensive instruments etc.

Accordingly, the present invention provides a process for the purification of Mitragynine or the process for obtaining purified Mitragynine salt.

The present process for purification of Mitragynine comprises first dissolving Mitragynine from crude Mitragynine extract in the solvent followed by adding acid in it to form precipitated salt, which is further purified with alcohol.

The inventors of the present invention have surprisingly found an improved process for the purification of Mitragynine or preparation of purified Mitragynine salt in high purity and high yield.

In one aspect of the invention, there is provided a process for the purification of Mitragynine comprising the steps of:

(a) adding crude extract of Mitragynine to a solvent in a reactor;
(b) stirring the mixture obtained in step (a);
(c) filtering the stirred solution obtained in step (b) to obtain filtered solution and spent;
(d) optionally, adding solvent to the spent obtained in step (c), followed by stirring and filtering, to obtain filtered solution;
(e) loading the filtered solution obtained in step (c) and/or step (d) into the reactor;
(f) adding a mixture of an acid and solvent to the filtered solution in the reactor of step (e);
(g) stirring the solution of step (f) until Mitragynine salt precipitate is formed;
(h) filtering the precipitated salt as obtained in step (g) followed by washing with solvent; and
(i) purifying the salt as obtained in step (h) with alcohol, followed by stirring, filtering and drying to form purified Mitragynine salt.

The crude extract of Mitragynine used in the present invention may be prepared by the methods known in the state of art. Traditionally known methods used for extraction of Mitragynine from plants includes maceration, percolation, reflux, Solvent Extraction, Soxhlet extraction. Amrianto et. al., *Mitragynine: a review of its extraction, identification, and purification methods, Current Research on Biosciences and Biotechnology* 3(1) 165-171, 2021, discloses various methods reported in the art for extracting Mitragynine, both conventional and renewable technology. Various extraction methods of Mitragynine reported in this literature are Solvent Extraction, Ultrasound assisted extraction (UAE), Accelerated solvent extraction (ASE) etc. The prepared crude extract of Mitragynine is purified by the process provided by the present invention.

The solvent employed in the steps (a) and (d) may be an organic solvent selected from a group comprising of chloroform, acetone, methanol, ethanol, n-butanol, isopropyl alcohol, ethyl acetate, diethyl ether, n-hexane, methylene dichloride, ethylene dichloride or mixture thereof, preferably the solvent is acetone.

In some embodiment of the invention, crude extract of Mitragynine is added slowly to the solvent with continuous mixing followed by stirring.

The stirring the mixture of crude extract of Mitragynine and solvent as mentioned in the step (b) may be carried out in 10 minutes to 4 hours, preferably 50 minutes to 3 hours, most preferably 2 hours, at 20-50 RPM, preferably 30-50 RPM.

In some embodiment of the invention, filtering the stirred solution of step (b) as mentioned in step (c) of the above-described process may be done as known in the state of art. In one preferred embodiment the stirred solution of step (b) is filtered through cleaned nutsche filter on 5 microns cloth. The said filtration step results in separation of filtered solution and spent.

The spent obtained in step (c) of the present process can optionally be treated again with solvent followed by stirring and filtering as defined above.

In one embodiment, the filtered solution obtained in step (c) is loaded into the reactor as mentioned in the step (e). In another embodiment, the filtered solution obtained in step (c) and step (d) are loaded into the reactor.

In some embodiment of the invention, the acid in step (f) is organic or mineral acid.

In some embodiment of the invention, the mixture of organic or mineral acid and solvent as used in the step (f) of the present invention is prepared by dissolving the organic or mineral acid in the solvent by stirring for 30 minutes-2 hours at 10-50 RPM, followed by filtering. In some embodiment of the invention, organic or mineral acid is added slowly to the solvent with continuous mixing followed by stirring for 1 hour at 30-50 RPM and filtering. Filtering may be done as known in the state of art or as described above. In one preferred embodiment filtration is carried through 100 mesh cloth.

The organic or mineral acid employed in the step (f) may be selected from a group comprising of hydrochloric acid, hydrobromic acid, perchloric acid, sulphuric acid, oxalic acid, tartaric acid, citric acid, formic acid, trifluoro acetic acid, trichloro acetic acid, or mixture thereof. In one preferred embodiment of the invention, the acid employed in step (f) of the above-described process is organic acid, most preferably oxalic acid.

The solvent employed in the step (f) may be an organic solvent selected from a group comprising of chloroform, acetone, methanol, ethanol, n-butanol, isopropyl alcohol, ethyl acetate, diethyl ether, n-hexane, methylene dichloride, ethylene dichloride or mixture thereof. In one preferred embodiment of the invention, the solvent employed in step (f) of the above-described process is acetone.

In some embodiment of the invention, as mentioned in steps (f) and (g) of the said process, the addition of mixture of organic or mineral acid and solvent to the filtered solution in the reactor of step (e) is followed by stirring until Mitragynine salt precipitate is formed.

The stirring as mentioned in the step (g) may be carried out in 10 minutes to 4 hours, preferably 50 minutes to 3 hours, most preferably 2 hours, at 20-50 RPM, preferably 30-50 RPM.

The Mitragynine salt precipitate as formed in step (g) depends upon the organic or mineral acid employed in the step (f). In one preferred embodiment of the invention, the Mitragynine salt precipitate formed in step (g) of the above-described process is hydrochloride salt, hydrobromide salt, perchlorate salt, sulphate salt, oxalate salt, tartrate salt, citrate salt, formate salt, trifluoro acetate salt, or trichloro acetate salt, most preferably oxalate salt.

In some embodiment of the invention, filtering the precipitated salt of step (g) as mentioned in step (h) of the above-described process may be done as known in the state of art. In one preferred embodiment the precipitated salt of step (g) is filtered through cleaned nutsche filter on 5 microns cloth.

In some embodiment of the invention, the precipitated salt after filtering as mentioned in the step (h) is washed with organic solvent to remove the impurities. The impurities as mentioned are mostly chlorophyll, plant matters, oils, resins or wax.

This step of washing with organic solvent may be performed multiple times till the desired colour as light greenish colour to light yellowish colour is obtained.

The organic solvent employed in the step (h) may be selected from a group comprising of chloroform, acetone, methanol, ethanol, n-butanol, isopropyl alcohol, ethyl acetate, diethyl ether, n-hexane, methylene dichloride, ethylene dichloride or mixture thereof. In one preferred embodiment of the invention, the organic solvent employed in step (h) of the above-described process is acetone.

In some embodiment of the invention, the purification of the precipitated salt of step (h) as mentioned in the step (i) is carried out in presence of alcohol. In some embodiment, the precipitated salt of step (h) is loaded into reactor and alcohol is added followed by stirring the mixture.

In one preferred embodiment the alcohol employed in step (i) is the dilute alcohol.

The alcohol employed in the step (i) may be selected from a group comprising of methanol, ethanol, propanol, butanol or mixture thereof. In one preferred embodiment of the invention, the alcohol employed in step (i) of the above-described process is methanol.

In some embodiment of the invention, the purification of the precipitated salt of step (h) as mentioned in the step (i) is carried out in presence of 5-20% methanol, preferably 5-15% methanol, most preferably 10% methanol.

The stirring the mixture of precipitated salt and alcohol as mentioned in the step (i) may be carried out in 50 minutes to 2 hours, most preferably 1 hour, at 20-50 RPM, preferably 30-50 RPM.

The filtration of the stirred solution as mentioned in step (i) of the above-described process may be done as known in the state of art. In one preferred embodiment the stirred solution of step (i) is filtered through cleaned nutsche filter on 5 microns cloth to separate the salt product.

The salt product obtained after filtration is dried by the processes as known in the state of art. Traditionally known methods for drying are sun drying, air drying, contact drying, infrared drying, freeze-drying, fluidized bed drying, dielectric drying etc.

In one preferred embodiment, the salt product obtained after filtration in step (i) of the present process is air dried for 2-10 hours and then loaded into Vacuum Tray Dryer at 45-50° C. under 700 mm of Hg to obtain high purity Mitragynine salt. Preferably the salt product obtained after filtration in step (i) of the present process is air dried for 5-6 hours and then loaded into Vacuum Tray Dryer to obtain high purity purified Mitragynine salt.

The purified Mitragynine salt obtained in step (i) of the present process is purified Mitragynine hydrochloride salt, purified Mitragynine hydrobromide salt, purified Mitragynine perchlorate salt, purified Mitragynine sulphate salt, purified Mitragynine oxalate salt, purified Mitragynine tartrate salt, purified Mitragynine citrate salt, purified Mitragynine formate salt, purified Mitragynine trifluoro acetate salt, or purified Mitragynine trichloro acetate salt, most preferably purified Mitragynine oxalate salt The present process is performed at room temperature.

In some embodiment of the invention there is provided a process for purification of Mitragynine, wherein said process comprises the steps of:

(a) adding crude extract of Mitragynine to acetone in the reactor;

(b) stirring the mixture obtained in step (a) for 2 hours at 30-50 RPM;

(c) filtering the stirred solution as obtained in step (b) to obtain filtered solution and spent;

(d) optionally, adding acetone to the spent obtained in step (c), followed by stirring and filtering, to obtain filtered solution;

(e) loading the filtered solution obtained in step (c) and/or step (d) into the reactor;

(f) adding a mixture of oxalic acid and acetone to the filtered solution in the reactor of step (e);

(g) stirring the solution of step (f) for 2 hours at 30-50 RPM, until Mitragynine oxalate salt precipitate is formed;

(h) filtering the precipitated Mitragynine oxalate salt as obtained in step (g) followed by washing with acetone; and (i) purifying the Mitragynine oxalate salt as obtained in step (h) with 10% Methanol, followed by stirring for 1 hour at 30-50 RPM, filtering and drying to form purified Mitragynine oxalate salt.

In some embodiment of the invention, crude extract of Mitragynine is added slowly to the acetone as defined above with continuous mixing followed by stirring for 2 hours at 30-50 RPM.

In some embodiment of the invention, the mixture of oxalic acid and acetone as used in the step (f) of the present invention is prepared by slowly adding oxalic acid to the acetone with continuous mixing followed by stirring for 1 hour at 30-50 RPM and filtering. In one preferred embodiment filtration is carried through 100 mesh cloth.

In some embodiment of the invention, the precipitated Mitragynine oxalate salt after filtering as mentioned in the step (h) is washed with acetone to remove the impurities. The impurities as mentioned are mostly chlorophyll, plant matters, oils, resins or wax.

In one preferred embodiment, the Mitragynine oxalate salt product obtained after filtration in step (i) of the present process is air dried for 5-6 hours and then loaded into Vacuum Tray Dryer at 45-50° C. under 700 mm of Hg, to obtain high purity Mitragynine oxalate salt.

The process of the present invention provides improved yield of Mitragynine oxalate salt (25%) with purity of 72-78% by HPLC.

In some embodiment of the invention, highly pure Mitragynine oxalate salt obtained according to present invention is suitable for the pharmaceutical preparations.

Certain specific aspect and embodiment of the present invention will be explained in detail with reference to the following examples, which are provided only for purposes of illustration and should not be construed as limiting the scope of the invention in any manner.

EXAMPLES

Example 1: Purification of Mitragynine

Crude Mitragynine Extract:

Crude Mitragynine extract can be obtained by traditionally known methods such as maceration, percolation, reflux, Solvent Extraction, Soxhlet extraction etc. For the present process, the crude extract of Mitragynine was obtained by the novel process for extraction of Mitragynine from *Mitragyna speciosa* plant, which is developed by the present inventor and is disclosed and filed separately in another Indian patent application No. IN 202341010687 filed in the Indian Patent Office on Feb. 17, 2023.

Treatment of Crude Mitragynine Extract with Acetone:

Acetone (720 litres) was added to the reactor. Crude Mitragynine extract (60 Kgs) was slowly added to the reactor and mixed with acetone followed by stirring for 2 hours at 30-50 RPM. The obtained solution is filtered through cleaned nutsche filter on 5 microns cloth to separate filtered solution and spent. Acetone (60 litres) was again added to the spent followed by stirring for 2 hours at 30-50 RPM and filtering through cleaned nutsche filter on 5 microns cloth to obtain filtered solution.

The filtered solution obtained above was combined and loaded into the cleaned reactor.

Preparation of Mixture of Oxalic Acid and Acetone:

Oxalic acid (12 Kgs) was added slowly to acetone (80 litres) with continuous mixing to allow oxalic acid to dissolve in acetone completely. This is followed by stirring for 1 hour at 30-50 RPM and filtering through 100 mesh cloth to obtain a mixture of oxalic acid and acetone.

Preparation of Precipitated Mitragynine Oxalate Salt:

The mixture of oxalic acid and acetone as obtained above was added to the filtered solution loaded into the cleaned reactor. The obtained solution was stirred for 2 hours at 30-50 RPM, until the Mitragynine oxalate salt precipitate is formed. The precipitate salt was filtered through cleaned nutsche filter on 5 microns cloth. The obtained salt after filtration was washed with fresh acetone (180-200 Litres) to remove the impurities and check for the colour from light greenish colour to light yellowish colour.

Purification of Mitragynine Oxalate Salt:

The obtained Mitragynine oxalate salt from the above method was loaded into the clean reactor. 10% of Methanol (500 Litres) was added to the reactor. The obtained solution was stirred for 1 hour at 30-50 RPM. The obtained salt solution is filtered through cleaned nutsche filter on 5 microns cloth. The resultant solid was air dried for 5 to 6 hours and then it was loaded into Vacuum Tray Dryer 45-50° C. under 700 mm of Hg to obtain purified off white coloured amorphous solid powder of Mitragynine oxalate salt.

All the steps are performed at room temperature.

Yield: 25%

Example 2: Purity of Obtained Salt by HPLC

The above process has been performed with 3 repetitions.

The obtained purified off white coloured amorphous solid powder of Mitragynine oxalate salt from 3 repetitions were analysed through HPLC for purity (FIGS. 1-3).

Purity: 75% by HPLC.

Other impurities: 7-OH Mitragynine, Paynanthenine, Speciogynine, and Speciolliatine.

What is claimed is:

1. A process for the purification of Mitragynine comprising the steps of:

(a) adding crude extract of Mitragynine to a solvent in a reactor;

(b) stirring the mixture obtained in step (a);

(c) filtering the stirred solution obtained in step (b) to obtain filtered solution and spent;

(d) optionally, adding solvent to the spent obtained in step (c), followed by stirring and filtering, to obtain filtered solution;

(e) loading the filtered solution obtained in step (c) and/or step (d) into the reactor;

(f) adding a mixture of an acid and solvent to the filtered solution in the reactor of step (e);

(g) stirring the solution of step (f) until Mitragynine salt precipitate is formed;

(h) filtering the precipitated salt as obtained in step (g) followed by washing with solvent; and (i) purifying the salt as obtained in step (h) with alcohol, followed by stirring, filtering and drying to form purified Mitragynine salt.

2. The process as claimed in claim 1, wherein in step (b) the stirring is carried out for about 2 hours at 30-50 RPM.

3. The process as claimed in claim 1, wherein in step (c) filtering is carried out through cleaned nutsche filter on 5 microns cloth.

4. The process as claimed in claim 1, wherein the acid in step (f) is organic or mineral acid.

5. The process as claimed in claim 4, wherein the mixture of organic or mineral acid and solvent in the step (f) is prepared by dissolving the organic or mineral acid slowly into the solvent with continuous mixing followed by stirring at 30-50 RPM for about 1 hour and filtering.

6. The process as claimed in claim 5, wherein filtering is carried out through 100 mesh cloth.

7. The process as claimed in claim 4, wherein the organic or mineral acid is selected from the group consisting of hydrochloric acid, hydrobromic acid, perchloric acid, sulphuric acid, oxalic acid, tartaric acid, citric acid, formic acid, trifluoro acetic acid and trichloro acetic acid or a mixture thereof.

8. The process as claimed in claim 7, wherein the organic or mineral acid is oxalic acid.

9. The process as claimed in claim 1, wherein the solvent employed in steps (a), (d), (f) and (h) is organic solvent selected from a group consisting of chloroform, acetone, methanol, ethanol, n-butanol, isopropyl alcohol, ethyl acetate, diethyl ether, n-hexane, methylene dichloride and ethylene dichloride or a mixture thereof.

10. The process as claimed in claim 1, wherein in steps (a), (d), (f) and (h) the solvent is acetone.

11. The process as claimed in claim 1, wherein in step (g) the stirring is carried out for about 2 hours at 30-50 RPM.

12. The process as claimed in claim 1, wherein the Mitragynine salt precipitate formed in step (g) is hydrochloride salt, hydrobromide salt, perchlorate salt, sulphate salt, oxalate salt, tartrate salt, citrate salt, formate salt, trifluoro acetate salt, or trichloro acetate salt.

13. The process as claimed in claim 1, wherein in step (g) the Mitragynine salt precipitate is Mitragynine oxalate salt precipitate.

14. The process as claimed in claim 1, wherein the alcohol in step (i) is dilute alcohol.

15. The process as claimed in claim 14, wherein the alcohol is selected from the group consisting of methanol, ethanol, propanol and butanol or a mixture thereof.

16. The process as claimed in claim 15, wherein the alcohol is methanol.

17. The process as claimed in claim 16, wherein the methanol is 10% methanol.

18. The process as claimed in claim 1, wherein in step (i) the stirring is carried out for about 1 hour at 30-50 RPM.

19. The process as claimed in claim 1, wherein in step (i) the salt product obtained after filtration is air dried for 5-6 hours followed by drying in Vacuum Tray Dryer at 45-50° C. under 700 mm of Hg.

20. The process as claimed in claim 1, wherein the purified Mitragynine salt obtained in step (i) is purified Mitragynine hydrochloride salt, purified Mitragynine hydrobromide salt, purified Mitragynine perchlorate salt, purified Mitragynine sulphate salt, purified Mitragynine oxalate salt, purified Mitragynine tartrate salt, purified Mitragynine citrate salt, purified Mitragynine formate salt, purified Mitragynine trifluoro acetate salt, or purified Mitragynine trichloro acetate salt.

21. The process as claimed in claim 1, wherein in step (i) the purified Mitragynine salt is purified Mitragynine oxalate salt.

22. The process as claimed in claim 21, wherein the obtained Mitragynine oxalate salt is in amorphous form.

23. The process as claimed in claim 21, wherein the purity of obtained Mitragynine oxalate salt is 72-78% by HPLC.

24. The process as claimed in claim 1, wherein said crude Mitragynine extract is obtained from *Mitragyna speciosa.*

25. A process for purification of Mitragynine comprising the steps of:

(a) adding crude extract of Mitragynine to acetone in the reactor;

(b) stirring the mixture obtained in step (a) for 2 hours at 30-50 RPM;

(c) filtering the stirred solution as obtained in step (b) to obtain filtered solution and spent;

(d) optionally, adding acetone to the spent obtained in step (c), followed by stirring and filtering, to obtain filtered solution;

(e) loading the filtered solution obtained in step (c) and/or step (d) into the reactor;

(f) adding a mixture of oxalic acid and acetone to the filtered solution in the reactor of step (e);

(g) stirring the solution of step (f) for 2 hours at 30-50 RPM, until Mitragynine oxalate salt precipitate is formed;

(h) filtering the precipitated Mitragynine oxalate salt as obtained in step (g) followed by washing with acetone; and (i) purifying the Mitragynine oxalate salt as obtained in step (h) with 10% Methanol, followed by stirring for 1 hour at 30-50 RPM, filtering and drying to form purified Mitragynine oxalate salt.

26. The process as claimed in claim 25, wherein the mixture of oxalic acid and acetone in step (f) is prepared by slowly adding oxalic acid to the acetone with continuous mixing followed by stirring for about 1 hour at 30-50 RPM and filtering through 100 mesh cloth.

27. The process as claimed in claim 25, wherein in step (i) the salt product obtained after filtration is air dried for 5-6 hours followed by drying in Vacuum Tray Dryer at 45-50° C. under 700 mm of Hg.

28. The process as claimed in claim 25, wherein the purity of obtained Mitragynine oxalate salt is 72-78% by HPLC.

29. The process as claimed in claim 25, wherein said crude Mitragynine extract is obtained from *Mitragyna speciosa.*

* * * * *